United States Patent [19]

Swaringen, Jr. et al.

[11] Patent Number: 4,568,744
[45] Date of Patent: Feb. 4, 1986

[54] BENZYLPYRIMIDINE SYNTHESIS AND INTERMEDIATES

[75] Inventors: Roy A. Swaringen, Jr., Durham; John F. Eaddy, III, Chapel Hill; Thomas R. Henderson, Raleigh, all of N.C.

[73] Assignee: Burroughs Wellcome Co., Research Triangle Park, N.C.

[21] Appl. No.: 609,593

[22] Filed: May 14, 1984

Related U.S. Application Data

[63] Continuation-in-part of Ser. No. 319,643, Nov. 7, 1981, abandoned.

[51] Int. Cl.⁴ ............................................ C07D 239/02
[52] U.S. Cl. .................................. 544/311; 544/320; 544/321; 544/323; 544/325; 544/334
[58] Field of Search ........................................ 544/311

[56] References Cited

U.S. PATENT DOCUMENTS

3,923,807  12/1975  Furukawa et al. .................. 544/311

FOREIGN PATENT DOCUMENTS

6051460  10/1979  Japan .
2019719  4/1970  Netherlands .

OTHER PUBLICATIONS

Kompis et al, Chem. Abst., 83:43376h.
Perun, Chem. Abst., 87:6009c.

Primary Examiner—Donald G. Daus
Assistant Examiner—Cecilia Shen
Attorney, Agent, or Firm—Donald Brown

[57] ABSTRACT

2,4-Diamino-5-(4-amino- and 4-loweralkylamino-3,5-disubstitutedbenzyl)pyrimidines are prepared by a novel method using 2,6-disubstituted anilines and pyrimidines. Several novel intermediates are involved.

2 Claims, No Drawings

BENZYLPYRIMIDINE SYNTHESIS AND INTERMEDIATES

This is a continuation-in-part of application Ser. No. 319,643 filed Nov. 7, 1981, now abandoned.

The present invention relates to a process for preparing a group of substituted 2,4-diamino-5-benzylpyrimidines.

German Patent Application No. 2 443 682 discloses inter alia compounds of the formula (I):

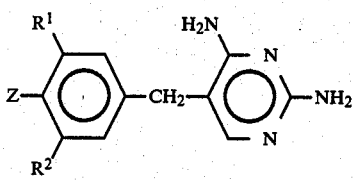

and salts thereof, wherein $R^1$ and $R^2$ are the same or different and each is $C_{1-3}$ alkyl, $C_{1-3}$ alkoxy, $C_{2-3}$ alkenyl or $C_{2-3}$ alkenyloxy and Z is amino or alkyl substituted amino. These compounds are described as having antibacterial activity and 2,4-diamino-5-(4-amino-3,5-dimethoxybenzyl)pyrimidine was subsequently disclosed as possessing good diuretic activity.

German Patent Application No. 2 634 358 discloses inter alia compounds of the formula (II):

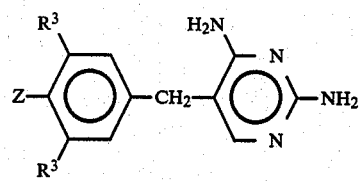

and salts thereof, wherein $R^3$ is a halogen atom and Z is amino or alkyl substituted amino. These compounds were also described as having antibacterial activity.

A novel synthesis of the compounds of the formulae (I) and (II) has now been discovered.

Accordingly, the present invention provides a process for the preparation of compound of the formula (III):

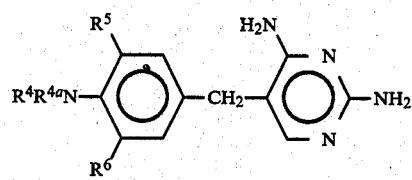

or a salt thereof, wherein $R^4$ and $R^{4a}$ are the same or different and each is a hydrogen atom or a $C_{1-4}$ alkyl group, $R^5$ is halogen, $C_{1-4}$ alkyl or $C_{1-4}$ alkoxy and $R^6$ is halogen, $C_{1-4}$ alkyl or $C_{1-4}$ alkoxy, which process comprises the reaction of a compound of the formula (IV):

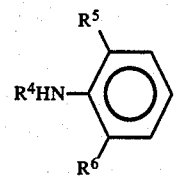

wherein $R^4$, $R^5$ and $R^6$ are as hereinbefore defined with (i) 2,4-diamino-5-hydroxymethylpyrimidine, or a $C_{1-4}$ ether thereof, (ii) formaldehyde and a secondary amino $R^7R^8NH$ to give a compound of the formula (V):

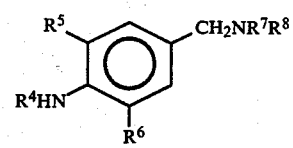

which is then reacted with a compound of the formula (VI):

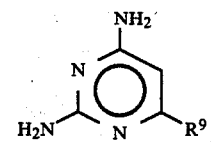

to give a compound of the formula (VII):

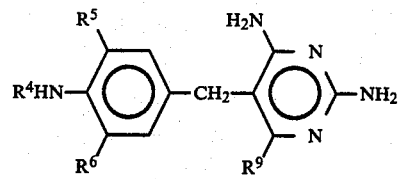

followed by the reductive removal of the group $R^9$ when $R^9$ is not hydrogen, wherein $R^4$, $R^5$ and $R^6$ are as hereinbefore defined, $R^7$ and $R^8$ are both $C_{1-4}$ alkyl or $R^7R^8NH$ represents morpholine or piperidine and $R^9$ is hydrogen, hydroxy, $C_{1-4}$ alkythio or mercapto, or (iii) 5-dimethylaminomethyluracil followed by the sequential alkylation of the amino group (where desired), halogenation and amination of the resultant uracil derivative of the formula (VIII):

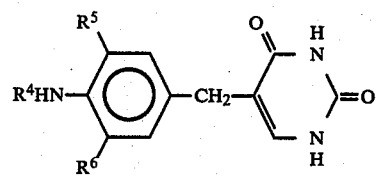

and thereafter, in any of variants (i), (ii) or (iii), optionally alkylating one compound of the formula (III) wherein $R^{4a}$ is hydrogen to give a compound of the formula (III) wherein $R^{4a}$ is $C_{1-4}$ alkyl.

This process is particularly suitable for the preparation of those compounds wherein $R^4$ is hydrogen. Suitably $R^5$ and $R^6$ are the same and each is methoxy, chlorine or $C_{1-4}$ alkyl.

Variation (i) of the process is suitably carried out in a solvent capable of dissolving both reactants; polar non-phenolic solvents are particularly suitable, at a non-extreme temperature, for example between 25° C. and 175° C. and preferably between 50° C. and 150° C. The reaction is preferably carried out in the presence of an acid, for example hydrochloric, acetic, methanesulphonic or p-toluenesulphonic acids. A preferred solvent is acetic acid.

The preparation of the compound of the formula (V) in variant (ii) of the process is carried out under the conditions described for the preparation of Mannich bases by Miocque and Vierfond (Bull. Soc. Chim. France 1970, 1896). The reaction is conveniently carried out in the presence of 0.5 mole of an acid, such as acetic acid, to 1 mole of each of the other ingredients. The compound of the formula (VI) is then reacted with a slight excess of the compound of the formula (V) in the presence of an acid such as p-toluenesulphonic acid. The reaction is normally carried out at an elevated temperature, suitably between 100° and 200° C. in a solvent having a suitably high boiling point, for example a glycol such as ethylene glycol. The dethiation is suitably carried out by hydrogenolysis in the presence of a transition metal catalyst. Raney nickel is particularly suitable for this process. This reaction is normally carried out in a polar solvent, for example a $C_{1-4}$ alkanol such as methanol or ethanol.

In variation (iii) the reaction of a compound of the formula (IV) with 5-dimethylaminomethyluracil is normally carried out in an inert high boiling polar solvent, for example a high boiling $C_{2-6}$ alkanol such as ethylene glycol, at between 100° and 200° C. for example between 130° and 160° C. The reaction is normally carried out under acidic conditions, for example in the presence of hydrochloric acid. The halogenation of the compound of the formula (VIII) and subsequent amination may conveniently be carried out by methods well known to those skilled in the art, for example by using the reaction conditions described in U.K. Pat. No. 875 562 or 1 132 082 or German Offenlegungschrift No. 2 258238.

The alkylation of the amino group in variant (iii) of the process is carried out under conditions, well known to those skilled in the art, that will not effect the uracil part of the molecule, for example, by the reaction of the amine with formic acid and the appropriate aldehyde. Preferably the reaction will be a methylation in which case the aldehyde will be formaldehyde. The optional alkylation of the amino group $NR^4H$ is carried out under conditions that will not effect the amino groups attached on the pyrimidine ring. Again suitable conditions are known to those skilled in the art, for example, the reaction with formic acid and the appropriate aldehyde.

The compounds of the formula (VII), (VIII) are novel intermediates and as such form an important part of the present invention. The compound of the formula (IX):

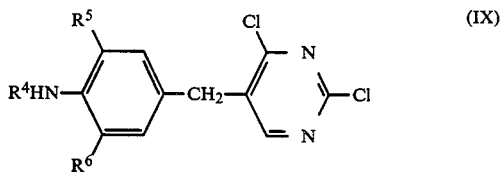

wherein $R^4$, $R^5$ and $R^6$ are as hereinbefore defined is also a novel intermediate forming part of the present invention.

EXAMPLE 1

Preparation of 2,6-Diisopropyl-4-piperidinomethylaniline

Following the conditions described by Miocque and Vierfond (Bull. Soc. Chim. France 1970, 1896), 2,6-diisopropylaniline (17.73 g, 0.10 mol), 37% aqueous formaldehyde (8.1 mL, 0.10 mol), piperidine (8.52 g, 0.10 mol), acetic acid (3.00 g, 0.05 mol), and ethanol (25 mL) were allowed to boil together until the temperature of the solution reached 92° C. The solution was then refluxed for 24 hours. The product was distilled under vacuum (122°–140° C. at 0.7–0.8 mm) to give the title compound (17.57 g, 64%).

$^1$H NMR (CDCl$_3$): $\delta$1.25 (d, 12, CH$_3$), 1.50 (m, 6, (CH$_2$)$_3$), 2.35 (m, 4, N(CH$_2$)$_2$), 2.95 (m, 2, CH), 3.35 (s, 2, Ar—CH$_2$), 3.70 (broad s, 2, NH$_2$), 7.0 (s, 2, Ar—H).

EXAMPLE 2

Preparation of 2,6-Diethyl-4-piperidinomethylaniline

A solution of 2,6-diethylaniline (29.85 g, 0.20 mol), 37% aqueous formaldehyde (16.2 mL, 0.20 mol), piperidine (17.03 g, 0.20 mol), acetic acid (6.00 g, 0.10 mol), and ethanol (25 mL) was reacted under conditions similar to Example 1.

The title compound (28.49 g, 57.8%) was isolated by vacuum distillation (115°–125° C. at 0.05 mm).

$^1$H NMR (CDCl$_3$): $\delta$1.25 (t, 6, CH$_3$), 1.50 (m, 6, (CH$_2$)$_3$), 2.35 (m, 4, N(CH$_2$)$_2$), 2.55 (q, 4, CH$_2$Me), 3.45 (s, 2, ArCH$_2$), 3.55 (broad s, 2, NH$_2$), 6.90 (s, 2, ArH).

EXAMPLE 3

Preparation of 2,6-Diisopropyl-4-(N,N-dimethylaminomethyl)aniline

A solution of 2,6-diisopropylaniline (35.45 g, 0.20 mol), 37% aqueous formaldehyde (16.2 mL, 0.20 mol), N,N-dimethylamine (9.02 g, 0.20 mol), acetic acid (6.00 g, 0.10 mol), and ethanol (25 mL) was reacted under conditions similar to Example 1.

The title compound (12.05 g, 26%) was isolated by vacuum distillation (112°–120° C., 0.2 mm).

$^1$H NMR (CDCl$_3$): $\delta$1.25 (d, 12, CH$_3$), 2.20 (s, 6, NMe$_2$), 2.95 (m, 2, CH), 3.35 (s, 2, ArCH$_2$), 3.70 (broad s, 2, NH$_2$), 7.0 (s, 2, ArH).

EXAMPLE 4

Preparation of 2,6-Diisopropyl-4-morpholinomethylaniline

A solution of 2,6-diisopropylaniline (35.45 g, 0.20 mol), 37% aqueous formaldehyde (16.2 mL, 0.20 mol), morpholine (17.42 g, 0.20 mol), acetic acid (6.00 g, 0.10 mol), and ethanol (25 mL) were reacted under conditions similar to Example 1. After concentration on the rotary evaporator, the residue was dissolved in diethyl ether and washed with aqueous sodium bicarbonate and water. After drying the ether solution, a solution of hydrogen chloride (0.20 mol) in ethanol was added. Filtration and drying gave the hydrochloride salt of the title compound (47.58 g, 76.0%). The salt (20.0 g, 0.6 mol) was dissolved in acetone and treated with solid potassium bicarbonate. Upon filtration and evaporation of solvent, the title compound was obtained (16.27 g, 92.2%).

Calculated for $C_{17}H_{28}N_2O$: C, 73.87; H, 10.21; N, 10.13. Found: C, 74.04; H, 10.31; N, 10.17.

EXAMPLE 5

Preparation of 2,4-Diamino-5-(4-amino-3,5-diisopropylbenzyl)-6-methylthiopyrimidine To 2,4-diamino-6-methylthiopyrimidine (1.56 g, 10.0 mmol) in ethylene glycol (50 mL) at 114° C. was added a solution of V ($R^4$=H, $R^5$=$R^6$=CHMe$_2$, $NR^7R^8$=morpholino, 3.32 g, 12.0 mmol) in ethylene glycol (25 mL) and p-toluenesulfonic acid monohydrate (0.19 g, 1.0 mmol). The temperature was maintained between 125° C. and 140° C. for 3¼ hours. The solvent was distilled in vacuo and 3N hydrochloric acid (20 mL) was added to the residue. The crude hydrochloride salt of the title compound (3.44 g, 90.0%) was dissolved in methanol, treated with charcoal, filtered, and evaporated until crystallization began. The slurry was diluted with isopropanol, filtered and dried to give the purified hydrochloride salt of the title compound (2.58 g, 68%).

The title compound was obtained by the addition of concentrated ammonium hydroxide (6 mL) to an aqueous solution of the hydrochloride salt (1.67 g, 4.37 mmol). Filtration and drying gave the title compound (1.38 g, 91.4%).

$^1$H NMR (CDCl$_3$): δ1.30 (d, 12, CH$_3$), 2.60 (s, 3, SCH$_3$), 3.0 (m, 2, CH), 3.6 (broad s, 2, ArNH$_2$), 3.35 (s, 2, ArCH$_2$), 4.7 (broad s, 4, NH$_2$), 7.0 (s, 2, ArH).

In a similar manner, VI ($R^9$=SCH$_3$, 1.56 g, 10.0 mmol) was reacted with V ($R^4$=H, $R^5$=$R^6$=CHMe$_2$, $NR^7R^6$=piperidino, 3.29 g, 12.0 mmol) to give the title compound (1.41 g, 41%).

Also, under similar conditions, VI ($R^9$=SCH$_3$, 1.56 g, 10.0 mmol) was reacted with V ($R^4$=H, $R^5$=$R^6$=CHMe$_2$, $R^7$=$R^8$=CH$_3$, 2.81 g, 12.0 mmol) to give the title compound (0.97 g, 28.4%).

EXAMPLE 6

Preparation of 2,4-Diamino-5-(4-amino-3,5-diisopropylbenzyl)pyrimidine

A solution of VII ($R^4$=H, $R^5$=$R^6$=CHMe$_2$, $R^9$=SCH$_3$, 0.50 g, 1.45 mmol) in methyl cellusolve (10 mL) and water (0.5 mL) was refluxed for six hours with T-1 Raney nickel (3 g). The solution was filtered and evaporated, and the residue triturated with hot hexane to give the title compound (0.36 g, 84%), m.p. 177°–180° C.

EXAMPLE 7

Preparation of 2,4-Diamino-5-(4-amino-3,5-diisopropylbenzyl)-6-hydroxypyrimidine A solution of VI·H$_2$O ($R^9$=OH, 1.44 g, 10.0 mmol), V ($R^9$=H, $R^5$=$R^6$=CHMe$_2$, $NR^7R^8$=morpholino, 3.32 g, 12.0 mmol), and p-toluenesulfonic acid monohydrate (0.19 g, 1.0 mmol) in ethylene glycol (75 mL) was heated for 4½ hours at 133°–138° C. The solvent was distilled under vacuum and 3N hydrochloric acid (20 mL) was added to the residue. The resulting hydrochloride salt was isolated, dissolved in water, and neutralized by the addition of concentrated ammonium hydroxide to give the title compound (2.36 g, 74.9%). The title compound was purified by recrystallization from ethanol (1.44 g, 45.7%).

$^1$H NMR (DMSO-d$_6$): δ1.05 (d, 6, CH$_3$), 2.90 (m, 2, CH), 3.30 (s, 2, ArCH$_2$), 4.15 (broad s, 2, ArNH$_2$), 5.45 (broad s, 2, NH$_2$), 4.15 (broad s, 2, NH$_2$), 6.80 (s, 2, ArH), 9.90 (s, 1, OH).

The title compound may be converted to VII ($R^9$=H) by sequential reaction with methanesulfonyl chloride to give VII ($R^9$=OSO$_2$Me), followed by catalytic hydrogenation with palladium to give VII ($R^9$=H), as, for example, in U.K. Pat. No. 1 542 804.

EXAMPLE 8

Preparation of 2,4-Diamino-5-(4-amino-3,5-diisopropylbenzyl)pyrimidine

A solution of VI ($R^9$=H, 1.10 g, 10.0 mmol), V ($R^4$=H, $R^5$=$R^6$=CHMe$_2$, $NR^7R^8$=morpholino, 3.32 g, 12.0 mmol), and p-toluenesulfonic acid monohydrate (0.19 g, 1.0 mmol) in ethylene glycol (50 mL) was heated for 5½ hours at 150°–160° C. The solvent was distilled under vacuum and 3N hydrochloric acid (20 mL) added to the residue. The resulting solution was washed with methylene chloride and evaporated to an oil which crystallized upon standing. The crystals were triturated with isopropanol, filtered, and dried to give the hydrochloride salt of the title compound (1.51 g, 45%), which was recrystallized from ethanol (1.04 g, 68.9%).

Addition of 3N sodium hydroxide to an aqueous solution of the hydrochloride salt (0.74 g, 2.20 mmol) gave the title compound (0.50 g, 76%).

$^1$H NMR (DMSO-d$_6$): δ1.15 (d, 12, CH$_3$), 2.95 (m, 2, CH), 3.50 (s, 2, ArCH$_2$), 4.50 (broad s, 2, ArNH$_2$), 6.15 (broad s, 2, NH$_2$), 6.55 (broad s, 2, NH$_2$), 6.80 (s, 2, ArH), 7.40 (s, 1, pyrimidine 5-H). M.p. 179°–182° C.

EXAMPLE 9

Preparation of 5-Dimethylaminomethyluracil Hydrochloride

Uracil (56.05 g, 0.50 mol) was refluxed with dimethylamine hydrochloride (81.55 g, 1.0 mol) and 37% aqueous formaldehyde (61 mL, 1.0 mol) in water (100 mL) for two days. The solvent was evaporated and the product triturated with methanol. After filtration and drying, the title compound was isolated (80.6 g, 78.3%).

$^1$H NMR (DMSO-d$_6$+D$_2$O): δ2.90 (s, 6, NMe$_2$), 4.10 (s, 2, NCH$_2$), 7.95 (s, 1, uracil 6-H).

EXAMPLE 10

Preparation of 5-(4-amino-3,5-diisopropylbenzyl)uracil

A mixture of 5-dimethylaminomethyluracil hydrochloride (10.28 g, 50.0 mmol) and 2,6-diisopropylaniline (10.64 g, 60.0 mmol) in ethylene glycol (75 mL) was heated for 4½ hours at 134°–137° C. After cooling, the title compound was filtered, washed with ethanol, and dried (5.55 g, 37%). A second crop was obtained from the mother liquor upon standing (3.24 g, 21.5%). The two crops were combined and recrystallized from methanol to give the purified title compound (5.84 g, 38.8%).

Calculated for $C_{17}H_{23}N_3O_2$: C, 67.75; H, 7.69; N, 13.94. Found: C, 67.59; H, 7.75; N, 13.88.

The title compound may be converted to VII ($R^4$=H, $R^5$=$R^6$=CHMe$_2$, $R^9$=H) via sequential halogenation and amination as described, for example, in U.K. Pat. No. 875 562 or 1 132 082, or German Offenlegungsschrift No. 2 258238.

EXAMPLE 11

Preparation of 2,4-Diamino-5-(4-amino-3,5-dimethoxybenzyl)pyrimidine

A mixture of 2,4-diamino-5-hydroxymethylpyrimidine (4.30 g, 30.0 mmol), prepared from 2,4-diamino-5-cyanopyrimidine as described in U.K. Pat. No. 1 413 472, 2,6-dimethoxyaniline (5.05 g, 33.0 mmol), acetic acid (60 mL), and concentrated hydrochloric acid (4.2 mL) was refluxed for 4½ hours, cooled, and filtered to give the hydrochloride salt of the title compound (7.13 g, 76.2%). The salt was dissolved in water and the solution made basic with concentrated ammonium hydroxide. The resulting precipitate was filtered, washed with water, and dried to give the title compound (5.18 g, 62.7%).

Calculated for $C_{13}H_{17}N_5O_2$: C, 56.72; H, 6.22; N, 25.44. Found: C, 56.63; H, 6.29; N, 25.39.

EXAMPLE 12

Other compounds of formula III prepared by variant (i) of this process are exemplified in Table I.

TABLE I

| | | | | Calculated (%) | | | Found (%) | | |
|---|---|---|---|---|---|---|---|---|---|
| $R^4$ | $R^5$ | $R^6$ | Yield, % | C | H | N | C | H | N |
| H | CHMe₂ | CHMe₂ | 55.1 | 68.19 | 8.42 | 23.39 | 68.08 | 8.49 | 23.17 |
| H | Et | Et | 61.4 | 66.39 | 7.80 | 25.81 | 66.14 | 8.03 | 25.71 |
| H | Me | Me | 70.7 | 64.17 | 7.05 | 28.78 | 63.94 | 6.97 | 28.79 |
| H | Me | Et | 63.3 | 65.34 | 7.44 | 27.21 | 65.03 | 7.49 | 27.11 |
| H | Me | CHMe₂ | 54.5 | 66.39 | 7.80 | 25.81 | 66.07 | 7.77 | 25.57 |
| H | Et | CHMeFT | 66.2 | 68.20 | 8.42 | 23.39 | 68.11 | 8.54 | 23.37 |
| H | Me | CMe₃ | 43.0 | 65.67 | 8.27 | 23.64 | 65.72 | 8.34 | 23.60[a] |
| H | Cl | Cl | 28.6 | 46.50 | 3.90 | 24.65 | 46.15 | 3.99 | 24.31 |
| H | Br | Br | 39.4 | 34.42 | 3.20 | 18.24 | 34.15 | 3.27 | 18.12[b] |
| H | Cl | Me | 60.1 | 54.65 | 5.35 | 26.55 | 54.45 | 5.32 | 26.33 |
| Et | Me | Me | 42.9 | 66.39 | 7.80 | 25.81 | 66.15 | 7.86 | 25.72 |

[a] Calculated for $C_{16}H_{23}N_5 \cdot 0.25\ H_2O \cdot 0.20$ MeOH. NMR confirms the presence and amount of MeOH. Karl Fisher analysis: 1.49% $H_2O$.
[b] Calculated for $C_{11}H_{11}Br_2N_5 \cdot 0.6\ H_2O$. Karl Fisher analysis: 2.9% $H_2O$.

EXAMPLE 13

Preparation of 2,4-Diamino-5-(3,5-dimethoxy-4-dimethylaminobenzyl)pyrimidine Dihydrochloride (A)
5-(4-Amino-3,5-dimethoxybenzyl)-2,4-(1H,3H)-pyrimidinedione A mixture of 10.04 g (49 mmol) of 5-[(dimethylamino)methyl]uracil hydrochloride (B. Roth, J. Z. Strelitz, and B. S. Rauckman, J. Med. Chem. 23, 379 (1980) and 7.48 g (49 mmol) of 2,6-dimethoxyaniline (m.p. 73°-74.5°; prepared from 2,6-dimethoxybenzoic acid by the procedure in Org. Reactions 3, 330 (1946)) in 50 mL of ethylene glycol under nitrogen was heated at 145° for 5 hours. The mixture was cooled and the precipitated solid was collected, suspended in 300 mL of boiling ethanol and collected to give 3.91 g (29%) of the title compound; m.p. 243°-245° (dec.).

Anal. Calc'd for $C_{13}H_{15}N_3O_4 \cdot \frac{1}{4}H_2O$: C, 55.41; H, 5.54; N, 14.91. Found: C, 55.46; H, 5.54; N, 14.94. A second crop 2.0 g (15%) was obtained by concentration of the ethanol extract.

(B)
5-(3,5-Dimethoxy-4-dimethylaminobenzyl)-2,4-(1H,3H)-pyrimidinedione

To a solution of 5-(4-amino-3,5-dimethoxybenzyl)-2,4-(1H,3e,uns/H/ )pyrimidinedione (5.4 g, 19.5 mmol) in 88% formic acid (70 mL) was added 37% formaldehyde (1.75 g). After refluxing 18 hrs, the reaction was cooled and 2 mL of conc. HCl were added. The solution was evaporated and the residue was dissolved in 200 mL of water. Neutralization of this solution with 5N sodium hydroxide gave 5.25 g (89%) of the title compound; m.p. 228°-230° (dec.).

Anal. Calc'd for $C_{15}H_{19}N_3O_4 \cdot 0.1H_2O$: C, 58.66; H, 6.30; N, 13.68. Found: C, 58.55; H, 6.30; N, 13.69.

(C)
2,4-Dichloro-5-(3,5-dimethoxy-4-dimethylaminobenzyl)pyrimidine

A mixture of 5.02 g (16.4 mmol) of 5-(3,5-dimethoxy-4-dimethylaminobenzyl)-2,4-(1H,3H)-pyrimidinedione in 100 mL of phosphoryl chloride was heated at reflux for 90 minutes. The excess $POCl_3$ was removed in vacuo and the residue was dissolved in dichloromethane and washed with aqueous sodium bicarbonate solution to neutrality, then with water. The solution was dried over $MgSO_4$, then passed through a silica gel column eluting with dichloromethane:methanol/19:1. The fractions containing product were combined and concentrated to an oil; 3.75 g (67%). The structure was confirmed by NMR.

(D)
2,4-Diamino-5-(3,5-dimethoxy-4-dimethylaminobenzyl)pyrimidine

A solution of 3.47 g (10.1 mmol) of 2,4-dichloro-5-(3,5-dimethoxy-4-dimethylaminobenzyl)pyrimidine in 200 mL of ethanol saturated with ammonia was heated in an autoclave at 150° for 8 hours. The solvent was removed in vacuo and the residue was triturated with water and collected. This was dissolved in dichloromethane:methanol/4:1, absorbed onto silica gel and placed at the top of a silica gel column. Elution with the same solvent gave 2.27 g (74%) of the title compound. A portion was converted to the dihydrochloride by recrystallization from 95% ethanol with conc. HCl; m.p. 228°-230° (dec.).

Anal. Calc'd for $C_{15}H_{21}N_5O_2 \cdot 2HCl \cdot H_2O$: C, 45.69; H, 6.39; N, 17.76; Cl, 17.98. Found: C, 45.70; H, 6.40; N, 17.77; Cl, 17.86.

We claim:

1. A compound of the formula (VIII)
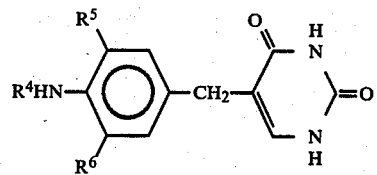
wherein $R^4$ is hydrogen or $C_{1-4}$ alkyl, and $R^5$ and $R^6$ are halogen, $C_{1-4}$ alkyl or $C_{1-4}$ alkoxy.
2. The compound of claim 1 in which $R^4$ is hydrogen and $R^5$ and $R^6$ are isopropyl.
* * * * *